(12) United States Patent
Clark et al.

(10) Patent No.: US 9,107,844 B2
(45) Date of Patent: Aug. 18, 2015

(54) TOPICAL SKIN TREATING COMPOSITIONS

(75) Inventors: Kathleen L. Clark, Medusa, NY (US); Jeffrey S. Reynolds, Durham, NC (US)

(73) Assignee: STIEFEL LABORATORIES INC., Coral Gables, FL (US)

( * ) Notice: Subject to any disclaimer, the term of this patent is extended or adjusted under 35 U.S.C. 154(b) by 1704 days.

(21) Appl. No.: 12/223,518

(22) PCT Filed: Feb. 2, 2007

(86) PCT No.: PCT/US2007/002900
§ 371 (c)(1),
(2), (4) Date: Feb. 13, 2009

(87) PCT Pub. No.: WO2007/092312
PCT Pub. Date: Aug. 16, 2007

(65) Prior Publication Data
US 2009/0226380 A1    Sep. 10, 2009

Related U.S. Application Data

(60) Provisional application No. 60/764,754, filed on Feb. 3, 2006.

(51) Int. Cl.
| A61K 8/38 | (2006.01) |
|---|---|
| A61K 8/67 | (2006.01) |
| A61K 31/327 | (2006.01) |
| A61Q 19/00 | (2006.01) |
| A61Q 17/04 | (2006.01) |
| A61K 8/22 | (2006.01) |

(52) U.S. Cl.
CPC . *A61K 8/38* (2013.01); *A61K 8/671* (2013.01); *A61K 31/327* (2013.01); *A61Q 19/008* (2013.01)

(58) Field of Classification Search
USPC .................. 424/45, 47, 59, 70.17, 401, 717; 514/24, 35, 36, 43, 356, 568
See application file for complete search history.

(56) References Cited

U.S. PATENT DOCUMENTS

| 4,497,794 | A | 2/1985 | Klein et al. |
|---|---|---|---|
| 4,609,674 | A | 9/1986 | Gupte |
| 5,089,509 | A | 2/1992 | Chandraratna |
| 5,242,433 | A | 9/1993 | Smith et al. |
| 5,254,109 | A | 10/1993 | Smith et al. |
| 5,368,581 | A | 11/1994 | Smith et al. |
| 5,417,674 | A | 5/1995 | Smith et al. |
| 5,446,028 | A | 8/1995 | Klein et al. |
| 5,449,519 | A | 9/1995 | Wolf et al. |
| 5,466,446 | A | 11/1995 | Stiefel et al. |
| 5,470,323 | A | 11/1995 | Smith et al. |
| 5,470,884 | A | 11/1995 | Corless et al. |
| 5,562,642 | A | 10/1996 | Smith et al. |
| 5,573,757 | A | 11/1996 | Riess et al. |
| 5,602,130 | A | 2/1997 | Chandraratna |
| 5,635,469 | A | 6/1997 | Fowler et al. |
| 5,660,839 | A | 8/1997 | Allec et al. |
| 5,690,923 | A | 11/1997 | DeVringer et al. |
| 5,707,635 | A | 1/1998 | Deckner et al. |
| 5,721,275 | A | 2/1998 | Bazzano |
| 5,733,886 | A | 3/1998 | Baroody et al. |
| 5,767,098 | A | 6/1998 | Klein et al. |
| 5,879,688 | A | 3/1999 | Coury et al. |
| 5,894,019 | A | 4/1999 | Hesse et al. |
| 5,914,334 | A | 6/1999 | Charu |
| 5,948,416 | A | 9/1999 | Wagner et al. |
| 5,976,565 | A | 11/1999 | Fotinos |
| 5,985,300 | A | 11/1999 | Crotty et al. |
| 5,993,787 | A | 11/1999 | Sun et al. |
| 6,001,380 | A | 12/1999 | Smith et al. |
| 6,013,637 | A | 1/2000 | Klein et al. |
| 6,017,549 | A | 1/2000 | Knight et al. |
| 6,017,938 | A | 1/2000 | Bershad |
| 6,048,902 | A | 4/2000 | Lebwohl et al. |
| 6,083,963 | A | 7/2000 | Bershad |
| 6,096,765 | A | 8/2000 | Bershad |
| 6,117,843 | A | 9/2000 | Baroody et al. |
| 6,193,956 | B1 | 2/2001 | Liu et al. |
| 6,280,764 | B1 | 8/2001 | Fotinos |
| 6,387,383 | B1 | 5/2002 | Dow et al. |
| 6,419,913 | B1 | 7/2002 | Niemiec et al. |
| 6,448,233 | B1 | 9/2002 | Lefevre et al. |
| 6,462,025 | B2 | 10/2002 | Vishnupad |
| 6,495,158 | B1 | 12/2002 | Buseman et al. |
| 6,517,847 | B2 | 2/2003 | Dow et al. |
| 6,635,676 | B2 | 10/2003 | Baker, Jr. et al. |
| 6,730,308 | B1 | 5/2004 | Sefton |
| 7,195,787 | B1 * | 3/2007 | Pykett et al. .................. 424/728 |
| 2002/0064541 | A1 | 5/2002 | Lapidot et al. |
| 2002/0110594 | A1 | 8/2002 | Vishnupad |
| 2002/0193321 | A1 | 12/2002 | Vishnupad et al. |

(Continued)

FOREIGN PATENT DOCUMENTS

| CA | 2015111 | 10/1991 |
|---|---|---|
| EP | 0729746 | 9/1996 |

(Continued)

OTHER PUBLICATIONS

Bath-Hextall et al., "Interventions for basal cell carcinoma of the skin: systematic review", BMJ online, Sep. 2004, vol. 329, No. 7468.

*Primary Examiner* — Jane C Oswecki
(74) *Attorney, Agent, or Firm* — Nath, Goldberg & Meyer; Joshua B. Goldberg

(57) ABSTRACT

A topical composition and methods of using same for treating various skin disorders or conditions. In a particular aspect, these compositions comprise a storage-stable benzoyl peroxide-containing composition in suspension and an antibiotic or pharmaceutically acceptable salt or ester thereof in solution and a retinoid or a pharmaceutically acceptable salt thereof in suspension, wherein the topical composition has a final pH of about 3 to about 8. In an alternative embodiment, these compositions comprise a storage-stable mixture of a retinoid or a pharmaceutically acceptable salt thereof and either a benzoyl peroxide-containing composition or clindamycin or a pharmaceutically acceptable salt thereof.

19 Claims, No Drawings

(56) References Cited

U.S. PATENT DOCUMENTS

| | | |
|---|---|---|
| 2003/0004118 A1 | 1/2003 | Vishnupad et al. |
| 2003/0044432 A1 | 3/2003 | Manetta et al. |
| 2003/0064097 A1 | 4/2003 | Patel et al. |
| 2003/0077301 A1 | 4/2003 | Maibach et al. |
| 2003/0170196 A1 | 9/2003 | Orsoni et al. |
| 2003/0215493 A1 | 11/2003 | Patel |
| 2004/0043946 A1 | 3/2004 | Popp |
| 2004/0157766 A1* | 8/2004 | Embil et al. ............. 514/1 |
| 2004/0167223 A1* | 8/2004 | Popp ..................... 514/568 |
| 2004/0171561 A1 | 9/2004 | Popp |
| 2005/0255130 A1 | 11/2005 | Vishnupad et al. |
| 2005/0255131 A1 | 11/2005 | Vishnupad et al. |

FOREIGN PATENT DOCUMENTS

| | | |
|---|---|---|
| GB | 1594314 | 7/1981 |
| GB | 2088717 | 6/1982 |
| WO | WO 92/17183 | 10/1992 |
| WO | WO 93/15726 | 8/1993 |
| WO | WO 01/91726 | 12/2001 |
| WO | WO 2007/002831 | 1/2007 |

\* cited by examiner

TOPICAL SKIN TREATING COMPOSITIONS

FIELD OF THE INVENTION

The present subject matter relates generally to a topical composition and methods of using same for treating various skin disorders or conditions. In a particular aspect, these compositions comprise a first storage-stable benzoyl peroxide-containing composition and a second composition comprising an antibiotic or pharmaceutically acceptable salt or ester thereof in solution and a retinoid or a pharmaceutically acceptable salt thereof in suspension. In an alternative embodiment, these compositions comprise a storage-stable mixture of a retinoid or a pharmaceutically acceptable salt thereof and either a benzoyl peroxide-containing composition or an antibiotic or a pharmaceutically acceptable salt thereof. In a third embodiment, these compositions comprise a storage-stable retinoid or a pharmaceutically acceptable salt thereof in suspension, and a storage stable mixture of benzoyl peroxide in suspension and an antibiotic or a pharmaceutically acceptable salt thereof in solution.

BACKGROUND OF THE INVENTION

Skin disorders involving the sebaceous glands and follicles in humans include conditions such as acne and rosacea, as well as other noninfectious dermatological diseases involving microorganisms. Such disorders are often marked by inflammation.

Acne is a common skin disorder characterized by blackheads, whiteheads, papules, pustules, cysts, and various sized nodules and scars which, in the inflammatory state of the disorder, are contaminated with bacteria such as *Propionibacterium acnes*. The disorder affects skin areas where the sebaceous glands are most active, and bacterial infection can occur in the sebaceous follicles.

In the past, these dermatological disorders have been treated with oral and/or topical antibacterial agents. The oral antibiotics used include tetracycline, erythromycin, and minocycline. The topical compositions used have separately contained the antibiotics tetracycline, erythromycin, and clindamycin; retinoids such as retinoic acid or tretinoin; and benzoyl peroxide, which exerts its antibacterial action via its potent oxidizing properties. However, the strong oxidizing properties of peroxide result in unstable compositions in which a peroxide is present. Benzoyl peroxide also can act as a sebosuppressant, an irritant, and a comedolytic agent.

One currently available product, Cleocin T® brand clindamycin topical solution by Pharmacia & Upjohn Company of Kalamazoo, Mich., is a topical solution containing 1% of clindamycin. Cleocin T®, however, has several drawbacks. For one, the formulation contains 50% isopropyl alcohol and water. This formulation often proves to be excessively drying and irritating to the skin. Second, the composition as dispensed by the pharmacist lacks the stability necessary for extended storage at room temperature.

Topical compositions combining at least two active antibacterial agents have been proposed as a treatment to these disorders. These compositions typically require compounding by the pharmacist and must be refrigerated. After three months of refrigeration, the compositions lose potency and effectiveness and must be replaced with a new batch.

For example, a currently available combination product is Benzamycin® brand topical gel (Dermik Laboratories, Berwyn, Pa.) which contains 3% of erythromycin and 5% of benzoyl peroxide. Benzamycin®, however, has several drawbacks. First, the product is supplied to pharmacies as a benzoyl peroxide gel in a first container and erythromycin powder in a second container. The product thus requires compounding by the pharmacist, who must (1) dissolve the erythromycin in alcohol, (2) add the erythromycin solution to the gel, and (3) stir until homogeneous in appearance. Second, the alcohol present in the composition as dispensed amounts to 16% of the total composition, which has proven to be excessively drying and irritating to the skin, particularly in combination with the benzoyl peroxide. Third, the composition as dispensed by the pharmacist (i.e., after reconstitution or compounding) lacks the stability necessary for extended storage at room temperature. The combination product can be stored under refrigeration for up to three (3) months.

Similarly, the currently available combination product BenzaClin® is a topical gel containing 1% of clindamycin and 5% of benzoyl peroxide. BenzaClin®, however, also has several drawbacks. For example, the product must be compounded by a pharmacist since it is supplied to pharmacies as a benzoyl peroxide gel in a first container and clindamycin powder in a second container. Accordingly, it lacks the stability necessary for extended storage at room temperature since the combined product can only be stored for up to two (2) months. By requiring compounding by pharmacists, it also has variability/impurity problems, which are the result of the drug forming partially dissolved or undissolved aggregates. This causes some patients to report that the product sometimes feels "gritty" when applied to the skin, further exacerbating the inflammation and irritation problem due to skin abrasion. Lastly, this composition must be topically applied at least twice a day to be effective in accordance with label directions.

As would be expected, compositions containing a combination of three of these active ingredients have proved to be even more difficult to manufacture than these compositions containing two active ingredients. Despite the inherent advantages to such triple active combinations, the difficulties in formulating a stable product have so far prevented the development of any products containing all three of an antibiotic, a retinoid, and benzoyl peroxide. Similarly, there have been many difficulties in formulating products containing a retinoid and either benzoyl peroxide or an antibiotic. Accordingly, there remains a need for such products for the treatment of various skin disorders, such as acne.

Other efforts at improving the stability of combination products in particular have relied on the use of novel packaging that keeps the active agents separated to maintain stability until the time of use. However, compounding is still necessary at the time of dispensing, and stability remains a problem because the product must be used immediately upon being prepared.

Another known topical composition for the treatment of acne is described in U.S. Pat. No. 6,117,843. This patent describes topical therapeutic compositions for the treatment of acne containing a combination of benzoyl peroxide and clindamycin. The clindamycin used in the disclosed compositions has a pre-combination pH of 5.9 to 6.9. Additionally, the disclosed compositions must be administered twice a day to be effective for the treatment of acne.

The presently known compositions for the treatment of acne are formulated for administration to patients twice per day and it has been reported that patient compliance with compositions that must be administered twice per day tends to be irregular, especially among teenagers who are the primary sufferers of acne.

Lastly, the current treatment options pose a significant risk of adverse side effects. Clindamycin, which is well absorbed through the skin, has been associated with colitis, diarrhea, and bloody diarrhea. Severe colitis may result in death. Likewise, benzoyl peroxide is a known skin-irritant that may not be well received by the skin. Similarly, retinoids also commonly are irritating, particularly to people with sensitive skin. Accordingly, there is a need to reduce the potential side effects of these prior compositions by reducing the number of required daily exposures to them.

For these reasons, it would be desirable to provide improved compositions and methods for formulating compositions for the treatment of acne. In particular, it would be desirable to provide products combining the activity of benzoyl peroxide with the activity of an antibiotic compound, such as clindamycin, and with the activity of a retinoid, with few or none of the disadvantages described above. Such compositions should overcome the formulation and stability problems which have been associated with the prior compositions, and provide improved compositions which are less irritating, easy to formulate, have a smooth consistency after formulation, are adequately stable, and have a sufficiently long storage life with or without refrigeration.

Similarly, it would likewise be desirable to provide products combining the activity of a retinoid with the activity of either an antibiotic compound, such as clindamycin, or with the activity of benzoyl peroxide, with few or none of the disadvantages described above. Such compositions should provide improved compositions which are less irritating, easy to formulate, have a smooth consistency after formulation, are adequately stable, and have a sufficiently long storage life with or without refrigeration.

Accordingly, there remains a need for a topical composition for the treatment of skin disorders that is storage-stable for an extended period of time, easy to formulate, and substantially uniform.

SUMMARY OF THE INVENTION

The present subject matter relates generally to topical compositions useful in treating various skin disorders or conditions.

An embodiment of the present inventive subject matter is directed to a topical composition for treating a skin disorder or condition, which comprises:
  a storage-stable benzoyl peroxide-containing composition in suspension, an antibiotic or pharmaceutically acceptable salt or ester thereof in solution, and a retinoid or a pharmaceutically acceptable salt thereof in suspension,
  wherein the topical composition has a final pH of about 3 to about 8.

In a preferred embodiment, the present subject matter relates to a topical composition for treating a skin disorder or condition, which comprises:
  a first storage-stable benzoyl peroxide-containing composition;
  a second composition comprising an antibiotic or pharmaceutically acceptable salt or ester thereof in solution and a retinoid or a pharmaceutically acceptable salt thereof in suspension,
  wherein the topical composition has a final pH of about 3 to about 8.

In a further preferred embodiment, the present subject matter also relates to a topical composition for treating a skin disorder or condition, which comprises:
  a storage-stable benzoyl peroxide-containing composition in suspension;
  an antibiotic or pharmaceutically acceptable salt or ester thereof in solution and a retinoid or a pharmaceutically acceptable salt thereof in suspension,
  wherein one or more of said benzoyl peroxide, said antibiotic or a pharmaceutically acceptable salt or ester thereof, and said retinoid or a pharmaceutically acceptable salt thereof is encapsulated or entrapped in a solid or a semi-solid ingredient, and
  wherein the topical composition has a final pH of about 3 to about 8.

In another preferred embodiment, the present subject matter relates to a topical composition for treating a skin disorder or condition, which comprises:
  a storage-stable benzoyl peroxide-containing composition in suspension;
  an antibiotic or pharmaceutically acceptable salt or ester thereof in solution and a retinoid or a pharmaceutically acceptable salt thereof in suspension,
  wherein said topical composition maintains a concentration of each of said benzoyl peroxide, said antibiotic or a pharmaceutically acceptable salt or ester thereof, and said retinoid or a pharmaceutically acceptable salt thereof ingredients that is at least 90% of a label claim for each of said ingredients.

In still another preferred embodiment, the present subject matter also relates to a method for treating a skin disorder or condition in a patient comprising topically administering to a patient in need thereof a topical composition in an amount effective to treat said skin disorder, wherein said composition comprises:
  a storage-stable benzoyl peroxide-containing composition in suspension;
  an antibiotic or pharmaceutically acceptable salt or ester thereof in solution and a retinoid or a pharmaceutically acceptable salt thereof in suspension,
  wherein the topical composition has a final pH of about 3 to about 8, and wherein the topical composition has a viscosity lower than the viscosity of the benzoyl peroxide-containing composition before mixing with said antibiotic/retinoid composition.

In a further preferred embodiment, the present subject matter relates to a topical composition for treating a skin disorder or condition, which comprises:
  a storage-stable benzoyl peroxide-containing composition in suspension;
  an antibiotic or pharmaceutically acceptable salt or ester thereof in solution and a retinoid or a pharmaceutically acceptable salt thereof in suspension,
  wherein the topical composition has a final pH of about 3 to about 8 that contributes to stability of said topical composition.

In yet another preferred embodiment, the present subject matter relates to a topical composition for treating a skin disorder or condition, which comprises:
  a storage-stable benzoyl peroxide-containing composition in suspension,
  an antibiotic or pharmaceutically acceptable salt or ester thereof in solution and a retinoid or a pharmaceutically acceptable salt thereof in suspension,
  wherein the topical composition is storage stable at room temperature of about 20-30° C. for at least 2 weeks.

In a further preferred embodiment, the present subject matter also relates to a topical composition for treating a skin disorder or condition, which comprises:
  a storage-stable mixture of 1) a retinoid or a pharmaceutically acceptable salt thereof, 2) either a benzoyl peroxide-containing composition or clindamycin or a pharmaceutically acceptable salt or ester thereof, and 3) a pharmaceutically acceptable carrier, wherein one or more of said retinoid or a pharmaceutically acceptable salt thereof, said benzoyl peroxide, and said clindamycin or a pharmaceutically acceptable salt thereof is encapsulated or entrapped in a solid or a semi-solid ingredient, and wherein the topical composition has a final pH of about 3 to about 8.

In another preferred embodiment, the present subject matter relates to a topical composition for treating a skin disorder or condition, which comprises:

a storage-stable mixture of 1) a retinoid or a pharmaceutically acceptable salt thereof, 2) either a benzoyl peroxide-containing composition or clindamycin or a pharmaceutically acceptable salt or ester thereof, and 3) a pharmaceutically acceptable carrier, wherein said topical composition maintains a concentration of each of said retinoid or a pharmaceutically acceptable salt thereof and said benzoyl peroxide or said clindamycin or a pharmaceutically acceptable salt or ester thereof ingredients that is at least 90% of a label claim for each of said ingredients.

In a further preferred embodiment, the present subject matter relates to a topical composition for treating a skin disorder or condition, which comprises:

a storage-stable mixture of 1) a retinoid or a pharmaceutically acceptable salt thereof, 2) either a benzoyl peroxide-containing composition or clindamycin or a pharmaceutically acceptable salt or ester thereof, and 3) a pharmaceutically acceptable carrier, wherein the topical composition has a final pH of about 3 to about 8 that contributes to stability of said topical composition.

In yet another preferred embodiment, the present subject matter relates to a topical composition for treating a skin disorder or condition, which comprises:

a storage-stable mixture of 1) a retinoid or a pharmaceutically acceptable salt thereof, 2) either a benzoyl peroxide-containing composition or clindamycin or a pharmaceutically acceptable salt or ester thereof, and 3) a pharmaceutically acceptable carrier, wherein the topical composition is storage stable at a refrigerated temperature of not more than 8° C. for about 6 months.

DETAILED DESCRIPTION OF THE INVENTION

Definitions

The term "acne" means a common inflammatory disease of the pilosebaceous glands characterized by comedones, papules, pustules, inflamed nodules, superficial pus-filled cysts, and (in extreme cases) canalizing and deep, inflamed, sometimes purulent sacs. Types of acne within the scope of the present subject matter include acne vulgaris or topical acne. "Acne" is caused by an interaction among hormones, keratin, sebum, and bacteria. One common bacterial causative agent is *Propionibacterium acnes*.

As used herein, the terms "administering", "administration", and like terms refer to any method which, in sound medical or cosmetic practice, delivers a composition to a subject in such a manner as to provide a positive effect on a dermatological disorder, condition, or appearance. The compositions are preferably administered such that they cover the entire area to be treated. "Direct administration" refers to any method which, in sound medical or cosmetic practice, delivers the composition to a subject without the use of another composition, delivery agent, or device. "Indirect administration" refers to any method which, in sound medical or cosmetic practice, delivers the composition to a subject with the use of at least one other composition, delivery agent, or device.

As used herein, the phrases an "effective amount" or a "therapeutically effective amount" of an active agent or ingredient, or pharmaceutically active agent or ingredient, which are synonymous herein, refer to an amount of the pharmaceutically active agent sufficient enough to have a positive effect on the area of application. Accordingly, these amounts are sufficient to modify the skin disorder, condition, or appearance to be treated but low enough to avoid serious side effects, within the scope of sound medical or dermatological advice. A therapeutically effective amount of the pharmaceutically active agent will cause a substantial relief of symptoms when applied repeatedly over time. Effective amounts of the pharmaceutically active agent will vary with the particular condition or conditions being treated, the severity of the condition, the duration of the treatment, the specific components of the composition being used, and like factors.

As used herein, the phrase an "extended period of time" refers to the shelf life of the presently preferred compositions, including time spent on the shelf at a pharmacy as well as the entire time period after sale of the composition during which the composition remains effective for the indicated use.

As used herein, the phrase a "label claim" refers to statements made on a label or literature accompanying a pharmaceutical product for sale. In this regard, the phrase "label claim" is intended to include indications on the label, packaging, and or literature of a pharmaceutical product of the amount(s) of any active ingredient(s) present in that product.

As used herein, the phrase "pharmaceutically acceptable salts" refers to salts of the active compound(s) which possess the same pharmacological activity as the active compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, naturally and synthetically derived amino acids.

Non-limiting examples of base salts include ammonium salts; alkali metal salts, such as podium and potassium salts; alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others. Water or oil-soluble or dispersible products are thereby obtained.

As used herein, the term "sensitivity" refers to the degree of skin irritation or skin inflammation, as exemplified by parameters in suitable assays for measuring sensitivity, inflammation, irritation, and the like. One such assay is the Jordan-King assay.

As used herein, the phrases "storage stable" or "storage-stable" are used interchangeably and refer to the ability of the present compositions to have a long shelf life, including time spent on the shelf at a pharmacy as well as the entire time period after sale of the composition, during which time the composition maintains its effectiveness and pharmaceutically acceptable appearance. Accordingly, the present compositions are stable in that they exhibit a minimum amount of degradation during an extended period of storage.

As used herein, a "treatment" or "treating" of a skin disease, disorder, or condition encompasses alleviation of at least one symptom thereof, a reduction in the severity thereof, or the delay, prevention, or inhibition of the progression thereof. Treatment need not mean that the disease, disorder, or condition is totally cured. A useful composition herein needs only to reduce the severity of a skin disease, disorder, or condition, reduce the severity of symptoms associated therewith, provide improvement to a patient's quality of life, or delay, prevent, or inhibit the onset of a skin disease, disorder, or condition.

Other terms as used herein are meant to be defined by their well-known meanings in the art.

Topical Compositions

The subject matter expressed herein relates generally to various topical compositions for treating a skin disorder, disease, or condition, and to methods for treating such skin diseases, disorders, or conditions using the same.

In one preferred aspect in this regard, the present subject matter relates to a topical composition for treating a skin disorder or condition, which comprises a first storage-stable benzoyl peroxide-containing composition and a second composition comprising an antibiotic or pharmaceutically acceptable salt or ester thereof in solution and a retinoid or a pharmaceutically acceptable salt thereof in suspension. In a preferred embodiment, the composition is formulated so that it has a final pH of about 3 to about 8. In another preferred embodiment, the benzoyl peroxide in the benzoyl peroxide-containing compositions is in suspension. In a further preferred embodiment, the antibiotic is clindamycin. In a still further embodiment, the first benzoyl peroxide-containing composition and second retinoid/antibiotic composition are stored separately, preferably in two separate chambers of a dual chamber device. In an even still further embodiment, the first retinoid composition and the second benzoyl peroxide/antibiotic composition are stored separately, preferably in two separate chambers of a dual chamber device.

In a particularly preferred embodiment of the present subject matter, the present compositions are formulated to have a viscosity lower than the viscosity of the benzoyl peroxide-containing composition before mixing with the antibiotic/retinoid composition. In an alternative particularly preferred embodiment, the present compositions are formulated so that one or more of the benzoyl peroxide, the antibiotic or a pharmaceutically acceptable salt or ester thereof, and the retinoid or a pharmaceutically acceptable salt thereof is encapsulated or entrapped in a solid or semi-solid ingredient.

In another alternative particularly preferred embodiment of the present subject matter, the present compositions are formulated to minimize the amount of degradates formed of the active ingredients present. In this regard, particularly preferred compositions herein are preferably capable of effectively maintaining a concentration of each of the benzoyl peroxide, antibiotic or a pharmaceutically acceptable salt or ester thereof, and retinoid or a pharmaceutically acceptable salt thereof ingredients that is at least 90% of a label claim for each of these ingredients.

A further alternative particularly preferred embodiment of the present subject matter relates to topical compositions containing each of these active ingredients at a final topical composition pH of about 3 to about 8 sufficient to contribute to product stability. Another alternative embodiment relates to combination compositions that are storage stable at a temperature of about 30° C. for about 2 weeks. In a still further alternative embodiment, the individual compositions in the topical compositions stored separately are storage stable at a temperature of 2-8° C., or up to 25 C for at least 6 months, with a projected shelf life of 2 years.

The benzoyl peroxide component of the present compositions is introduced in an initial benzoyl peroxide-containing composition formed as a solution, dispersion, or suspension, preferably as a suspension. The benzoyl peroxide is pharmaceutical grade. This benzoyl peroxide may be in the form of a slurry of a finely divided powder, or in the form of a hydrous granular material which may have its particle size reduced accordingly during processing according to the present subject matter. Preparation of suitable benzoyl peroxide constituents is well described in the medical and patent literature.

The benzoyl peroxide component of the present compositions is generally present at an amount of between about 0.1% to about 25% by weight of the total topical composition. In a preferred embodiment, the compositions contain benzoyl peroxide from about 0.5% to about 5% by weight of the total topical composition. Additionally, the present compositions are unique in that they are preferably capable of effectively maintaining a level of benzoyl peroxide that is at least 90% of the label claim for the benzoyl peroxide.

According to this embodiment, the initial benzoyl peroxide-containing composition, prior to mixing, has a preferred viscosity of about 25,000 to about 1,250,000 centipoises.

In another preferred embodiment, the particle size of the benzoyl peroxide can be reduced prior to inclusion in the present compositions. Such reduction in particle size can be carried out through processing, such as processing involving a milling process, or the use of solvents.

The antibiotic component of the antibiotic/retinoid composition of the present subject matter is preferably clindamycin. The antibiotic component of the present compositions is preferably a pharmaceutical grade salt or ester of clindamycin. Pharmaceutically acceptable salts, esters, or solvates of clindamycin refer to those which possess the desired pharmacological activity and which are neither biologically nor otherwise undesirable. Clindamycin phosphate (ester) and clindamycin hydrochloride (salt) are preferred pharmaceutically acceptable salts and esters of clindamycin which can be used in the present compositions due to their compatibility with gelling agents and extensive history of topical use. However, other suitable antibiotics discussed herein are also possible alternatives for the antibiotic component of the antibiotic/retinoid composition.

The antibiotic component of the present compositions is introduced in an initial antibiotic/retinoid containing, or antibiotic-containing composition as a solution, dispersion, or suspension, preferably as a solution. The antibiotic component of the present compositions is generally present at an amount of from about 0.5% to about 3% by weight of the total topical composition. Additionally, the present compositions are unique in that they are preferably capable of effectively maintaining a level of antibiotic that is at least 90% of the label claim for the clindamycin.

The retinoid component of the present compositions is preferably a pharmaceutical grade salt of the retinoid. Pharmaceutically acceptable salts, esters, or derivatives of retinoids refer to those which possess the desired pharmacological activity and which are neither biologically nor otherwise undesirable. The retinoid component of the present compositions is generally present at an amount of from about 0.01% to about 1.5% by weight of the total topical composition. In a particularly preferred embodiment, the retinoid is present at an amount of about 0.01% to about 0.5% by weight of the total topical composition. The retinoid component of the present compositions is introduced in an initial antibiotic/retinoid containing, or retinoid-containing composition formed as a solution, dispersion, or suspension, preferably as a suspension.

Additionally, the present compositions are unique in that they are preferably capable of effectively maintaining a level of retinoid that is at least 90% of the label claim for the retinoid.

Any of a wide variety of retinoids known as useful in treating skin diseases, disorders, or conditions is contemplated as capable of being included in the present compositions. Retinoids available for use in the present inventive subject matter include all natural and synthetic retinoids. In this regard, preferred non-limiting examples of retinoids useful in the present compositions include tazarotene, retinoic acid, tretinoin, isotretinoin, adapalene, bexarotene, alitretinoin, vitamin A, retinol, retinal, retinyl palmitate, retinyl acetate, ethyl 5-(2-(4,4-dimethylthiochroman-6-yl)ethynyl)thiophene-2-carboxylate, 6-(2-4,4-dimethylthiochroman-6-yl)-ethynyl)-3-pyridylmethanol, 2-(2-(4,4-dimethylthiochroman-6-yl)-ethynyl)-5-pyridinecarboxaldehyde, salts thereof, derivatives thereof, and mixtures thereof. Tazarotene, retinoic acid, tretinoin, and isotretinoin, as well as salts or derivatives thereof, are especially preferred in this regard. In a most preferred embodiment, the retinoid is tazarotene or a salt or derivative thereof.

In preferred embodiments, one or more of the benzoyl peroxide, antibiotic or a pharmaceutically acceptable salt or ester thereof, and retinoid or a pharmaceutically acceptable salt thereof in the present compositions is encapsulated or entrapped in a solid or semi-solid ingredient for inclusion in the final compositions. This encapsulation of the active ingredient(s) can help prevent reactions between the retinoid, antibiotic, and benzoyl peroxide components, thus promoting the storage-stability of each of these ingredients and of the topical composition as a whole.

In further preferred embodiments, this solid or semi-solid ingredient has a melting point at about a mammal's body temperature, such as a human's body temperature. Specific solid and semi-solid ingredients useful in this regard are well known to those of ordinary skill in the art, such as those described in *The Merck Index*, Thirteenth Edition, Budavari et al., Eds., Merck & Co., Inc., Rahway, N.J. (2001); the CTFA (Cosmetic, Toiletry, and Fragrance Association) *International Cosmetic Ingredient Dictionary and Handbook*, Tenth Edition (2004); and the "Inactive Ingredient Guide", U.S. Food and Drug Administration (FDA) Center for Drug Evaluation and Research (CDER) Office of Management, http://www.accessdata.fda.gov/scripts/cder/iig/index.cfm, the contents of which are hereby incorporated by reference in their entirety.

Similarly, in a preferred embodiment one or more of the benzoyl peroxide, antibiotic or a pharmaceutically acceptable salt or ester thereof, and retinoid or a pharmaceutically acceptable salt thereof can be present in the final topical composition in a solution, suspension, or dispersion. Preferably, the benzoyl peroxide component and retinoid component are present as suspensions, while the antibiotic component is present as a solution.

Once all of the ingredients are combined, the preferred final compositions herein have a final viscosity of about 20,000 to about 1,000,000 centipoises. In a particularly preferred embodiment, the final compositions have a final viscosity of about 40,000 to about 500,000 centipoises. This final viscosity that is lower than the viscosity of the initial benzoyl peroxide-containing compositions demonstrates that the present compositions are easier to mix together, contain less degradates, and have a greater degree of uniformity than those compositions previously known in the art.

In a preferred embodiment, the final topical compositions exhibit a final pH of about 3 to about 8. In a particularly preferred embodiment, the present compositions exhibit a final pH of about 3.5 to about 5.5. In a most preferred embodiment, the present compositions exhibit a final pH of about 4 to about 5 as a target. This narrowly tailored pH is in part responsible for the advanced storage stability of the present compositions in comparison to those previously known in the art. In this regard, the present preferred compositions can remain storage stable at a temperature of up to about 25° C. for up to about 30 days, or more. In a particularly preferred embodiment, the present compositions can remain storage stable at a temperature of up to about 30° C. for at least 14 days.

In an alternative preferred embodiment, the present compositions can remain storage stable at a refrigerated temperature of not more than 15° C. for at least 60 days. In a particularly preferred embodiment in this regard, the present compositions can remain storage stable at a refrigerated temperature of about 2° C. to about 8° C. for at least 6 months. When the separately stored compositions of the topical compositions are stored at a temperature of 2-8° C., or up to 25° C., the separate compositions are stable for up to about 6 months, with a projected shelf life of about 2 years.

In another alternative embodiment, the present compositions can remain storage stable when stored separately under conditions selected from the group consisting of freezer conditions of less than about 0° C., about 2° C. to about 8° C., about 8° C. to about 15° C., about 23° C. to about 27° C., up to about 25° C., and about 15° C. to about 30° C.

The present preferred compositions do not require compounding at the time of dispensing and maintain stability for extended periods depending on the storage temperature, despite the relative incompatibility of the benzoyl peroxide, clindamycin, and retinoid. This represents a distinct advantage over the formulations presently known in the art.

The present compositions may be formulated for either once-per-day or twice-per-day administration. In a preferred embodiment, the once-per-day administration is in the evening or at night to increase compliance and to account for skin conditions most favorable to reducing inflammation.

The initial benzoyl peroxide-containing composition, as well as the final composition, may take the form of a solution, gel, cream, lotion, suspension, emulsion, ointment, spray, foam, paste, or any combination thereof. Preferably, the initial benzoyl peroxide-containing composition is in the form of a suspension. Other cosmetic treatment compositions known to those skilled in the art, including liquids and balms, are additionally contemplated as falling within the scope of the present subject matter.

Emulsions, such as oil-in-water or water-in-oil systems, as well as a base (vehicle or carrier) for the topical formulation can be selected to provide effectiveness of the active ingredients and/or avoid allergic and irritating reactions (e.g., contact dermatitis) caused by ingredients of the base or by the active ingredients.

Accordingly, the present compositions may optionally further comprise an emulsifier. Non-limiting examples of emulsifiers useful in this regard include glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, tragacanth gum, poly(acrylamide-b-acrylic acid), 10-30 alkyl acrylate crosspolymers, derivatives thereof, and mixtures thereof.

Creams useful in the present compositions may also be semisolid emulsions of oil and water and are easily applied and vanish when rubbed into the skin.

Lotions useful in the present compositions include older definitions such as suspensions of powdered material (e.g., calamine) in a water or alcohol base, as well as modern lotions (e.g., some corticosteroids) such as water-based emulsions. Convenient to apply, lotions are also cool and help to dry acute inflammatory and exudative lesions.

Ointments which are useful are oleaginous and contain little if any water; feel greasy but are generally well tolerated; best used to lubricate, especially if applied over hydrated skin; they are preferred for lesions with thick crusts, lichenification, or heaped-up scales and may be less irritating than cream for some eroded or open lesions (e.g., stasis ulcers). Drugs in ointments are often more potent than in creams.

In a preferred embodiment, the present compositions may take the form of a gel. In this regard, the present compositions may include a gelling agent and/or a thickener. Suitable gelling agents and/or thickeners which may be useful in the present compositions include aqueous thickening agents, such as neutral, anionic, and cationic polymers, and mixtures thereof. Exemplary polymers which may be useful in the instant compositions include carboxy vinyl polymers, such as carboxypolymethylene. A preferred thickener is a carbomer, for example Carbopol® brand Carbopol polymer such as is available from Noveon Inc., Cleveland, Ohio. Other exemplary polymers useful in this regard include hydrophilic/hydrophobic graft copolymers, such as polymers formed as a mixture of polystyrene/microsponge/Carbopol®. One such polymer in this regard is a dimethylacrylamide/acrylic acid/polystyrene ethyl methacrylate copolymer, for example Pharmadur® brand copolymer such as is available from Polytherapeutics, Inc., Bridgewater, N.J.

Other, non-limiting example of suitable thickeners useful herein include cellulosic polymers, such as gum arabic, gum acacia, gum tragacanth, locust bean gum, guar gum, hydroxypropyl guar, xanthan gum, cellulose gum, sclerotium gum, carageenan gum, karaya gum, cellulose gum, rosin, methylcellulose, hydroxyethylcellulose, hydroxypropylcellulose, hydroxymethylcellulose, hydroxypropylmethylcellulose, methylhydroxyethylcellulose, cetyl hydroxyethylcellulose, carboxymethylcellulose, corn starch, hydroxypropyl starch phosphate, distarch phosphate, distarch dimethylene urea, aluminum starch octenyl succinate, maltodextrin, dextran, poly(acrylamide), PEG-150 distearate, PEG-150/decyl alcohol/SMDI copolymer, PEG-150/stearyl alcohol/SMDI copolymer, PEG-180/Laureth-50/TMMG copolymer, Polyether 1, acrylic acid/acrylamidomethyl propane sulfonic acid copolymer, acrylate/C10-30 alkyl acrylate crosspolymer, acrylate/beheneth-25 methacrylate copolymer, acrylate/steareth-20 methacrylate copolymer, acrylate/steareth-20 copolymer, acrylate/VA crosspolymer, acrylic acid/acrylonitrogen copolymer, ammonium acryloyldimethyltaurate/beheneth-25 methacrylate copolymer, ammonium acryloyldimethyltaurate/VP copolymer, caprylic/capric triglyceride (and) sodium acrylate copolymer, PVM/MA decadiene crosspolymer, alginic acid, propylene glycol alginate, dimethicone, silica dimethyl silylate, a dimethylacrylamide/acrylic acid/polystyrene ethyl methacrylate copolymer, derivatives thereof, and mixtures thereof. Other common thickeners and/or gelling agents, such as polyacrylic polymers, may be further useful herein. These thickeners and/or gelling agents can be present in the instant compositions regardless of what form the final composition takes.

Any other non-toxic, inert and effective carrier may be used to formulate the present preferred compositions. Well-known carriers used to formulate other therapeutic compounds for administration to humans particularly will be useful in the compositions of the present subject matter. Pharmaceutically acceptable carriers, excipients and diluents in this regard are well known to those of skill in the art, such as those described in *The Merck Index*, Thirteenth Edition, Budavari et al., Eds., Merck & Co., Inc., Rahway, N.J. (2001), which is incorporated by reference herein in its entirety. Examples of such useful pharmaceutically acceptable excipients, carriers and diluents include distilled water, physiological saline, Ringer's solution, dextrose solution, Hank's solution and DMSO, which are among those preferred for use in the present subject matter.

These additional components, as well as effective formulations and administration procedures are well known in the art and are described in standard textbooks, such as *Goodman and Gillman's: The Pharmacological Bases of Therapeutics*, 8th Ed., Gilman et al. Eds. Pergamon Press (1990) and *Remington's Pharmaceutical Sciences*, 17th Ed., Mack Publishing Co., Easton, Pa. (1990), both of which are incorporated by reference herein in their entirety.

Examples of preferred excipients that can be used according to the present preferred compositions include but are not limited to a carbomer, a polyacrylic polymer, glycerin, sodium hydroxide, sodium thiosulfate, propyl gallate, an alkyl paraben, purified water, titanium dioxide, zinc oxide, and mixtures thereof.

Other ingredients which may optionally be provided in the instant topical compositions include humectants, such as propylene glycol; solvents, such as alcohol (de minimis); sun filters, such as titanium dioxide, zinc oxide, and mixtures thereof; and anti-microbial preservatives, such as methylparaben and propylparaben. The topical compositions may also include an organic or inorganic base, such as sodium hydroxide, which is used to adjust the pH of the initial components and the final product.

In this regard, the preferred compositions discussed herein can additionally comprise remaining amounts of one or more dermatologically acceptable excipients. Preferred, non-limiting examples of dermatologically acceptable excipients useful in these compositions are those selected from the group consisting of surfactants, preservatives, emollients, humectants, fluid alkyl alcohols, thickening agents, emulsifiers, suspending agents, pH modifiers/buffering agents, chelating agents, antioxidants, sun filters, derivatives thereof, and mixtures thereof.

Accordingly, any surfactant, preservative, emollient, humectant, fluid alkyl alcohol, thickening agent, emulsifier, suspending agent, pH modifier, chelating agent, antioxidant, sun filter, or other dermatologically acceptable excipient commonly known to those of ordinary skill in the art as useful in topical compositions is contemplated as useful in the compositions described herein. Further, any non-toxic, inert, and effective topical carrier may be used to formulate the compositions described herein. Well-known carriers used to formulate other topical therapeutic compositions for administration to humans will be useful in these compositions. Examples of these components that are well known to those of skill in the art are described in *The Merck Index*, Thirteenth Edition, Budavari et al., Eds., Merck & Co., Inc., Rahway, N.J. (2001); the CTFA (Cosmetic, Toiletry, and Fragrance Association) *International Cosmetic Ingredient Dictionary and Handbook*, Tenth Edition (2004); and the "Inactive Ingredient Guide", U.S. Food and Drug Administration (FDA) Center for Drug Evaluation and Research (CDER) Office of Management, http://www.accessdata.fda.gov/scripts/cder/iig/index.cfm, the contents of which are hereby incorporated by reference in their entirety.

In severe cases, occlusive therapy may be useful where acne is present concurrently with other indications or conditions such as psoriasis, atopic dermatitis, lupus erythematosus, and chronic hand dermatitis. Covering the treated area with a nonporous occlusive dressing can increase the absorption and effectiveness of the present compositions. Usually, a polyethylene film (plastic household wrap) is applied overnight over cream or ointment, which tends to be less irritating than lotion for occlusive therapy. Plastic tapes may be impregnated with drug and is especially convenient for treating isolated or recalcitrant lesions; children and (less often) adults may experience pituitary and adrenal suppression after prolonged occlusive therapy over large areas.

The present inventive subject matter further relates to a topical composition for treatment of a skin disorder or condition comprising a first composition comprising benzoyl peroxide and an antibiotic or a pharmaceutically acceptable salt or ester thereof, preferably clindamycin or a pharmaceutically acceptable salt or ester thereof, and a second composition comprising a retinoid or a pharmaceutically acceptable salt or ester thereof. Preferably, the first composition and the second composition in this embodiment are stored separately. More preferably, the first composition and second composition are stored in separate chambers of a dual chamber apparatus. In addition, it is preferable that the benzoyl peroxide in the first composition is in suspension, while the antibiotic in the first composition is in solution, while the retinoid in the second composition is in suspension.

In an alternative embodiment, the present subject matter further relates to a topical composition for treating a skin disorder or condition, which comprises a storage-stable mixture of 1) a retinoid or a pharmaceutically acceptable salt thereof, 2) either a benzoyl peroxide-containing composition or clindamycin or a pharmaceutically acceptable salt or ester thereof, and 3) a pharmaceutically acceptable carrier. In a preferred embodiment, the composition is formulated so that it has a final pH of about 3 to about 8. Preferably, the retinoid composition and the benzoyl peroxide-containing composition or clindamycin composition are stored in separate chambers of a dual chamber apparatus.

In particular, the present inventive subject matter relates to a topical composition for treating a skin disorder or condition, which comprises a storage-stable mixture of 1) a retinoid or a pharmaceutically acceptable salt thereof, 2) a benzoyl peroxide-containing composition, and 3) a pharmaceutically acceptable carrier. Preferably, the retinoid composition and the benzoyl peroxide-containing composition are stored in separate chambers of a dual chamber apparatus or other storage apparatus in which the two compositions are stored separately prior to application.

In a further alternative embodiment, the present subject matter further relates to a topical composition for treating a skin disorder or condition, which comprises a storage-stable mixture of 1) a retinoid or a pharmaceutically acceptable salt thereof, 2) a clindamycin or a pharmaceutically acceptable salt or ester thereof, and 3) a pharmaceutically acceptable carrier. In a preferred embodiment, the retinoid is in suspension and the clindamycin is in solution. Preferably, the retinoid composition and the clindamycin-containing composition are stored in separate chambers of a dual chamber apparatus.

In a still further preferred embodiment, the present inventive subject matter relates to a topical composition for treating a skin disorder or condition, which comprises a storage-stable mixture of 1) a clindamycin or a pharmaceutically acceptable salt or ester thereof in solution form, and 2) a benzoyl peroxide-containing composition in suspension. Preferably, the clindamycin composition and the benzoyl peroxide-containing composition are stored in separate chambers of a dual chamber apparatus or other storage apparatus in which the two compositions are stored separately prior to application.

Additional Active Ingredients

In addition to the benzoyl peroxide, antibiotic, and retinoid, the present compositions may further contain other active ingredients readily known to those of skill in the art as useful in the topical treatment of skin disorders or conditions. Exemplary additional active ingredients include, but are not limited to, additional macrolide antibiotics, bactericidal drugs, bacteriostatic drugs, cleansing agents, absorbents, anti-infective agents, anti-inflammatory agents, astringents (drying agents that precipitate protein and shrink and contract the skin), emollients (skin softeners), moisturizers, keratolytics (agents that soften, loosen, and facilitate exfoliation of the squamous cells of the epidermis), and mixtures thereof.

Exemplary macrolide antibiotics contemplated as within the scope of the present subject matter include, but are not limited to, Azithromycin, Clarithromycin, Erythromycin, Lincomycin, and mixtures thereof. The macrolides are similar in structure and activity. All the macrolides are easily absorbed and all are primarily bacteriostatic and bind to the 50S subunit of the ribosome, thus inhibiting bacterial protein synthesis. These drugs are active against aerobic and anaerobic gram-positive cocci, with the exception of enterococci, and against gram-negative anaerobes and useful in the present compositions.

Exemplary bactericidal drugs (i.e., kill bacteria) contemplated as within the scope of the present subject matter include, but are not limited to, Penicillins, cephalosporins, vancomycin, aminoglycosides, quinolones, and polymyxins.

Exemplary bacteriostatic drugs (i.e., slow bacterial growth) contemplated as within the scope of the present subject matter include, but are not limited to, erythromycin, tetracyclines, chloramphenicol, lincomycin, clarithromycin, azithromycin, and sulfonamides. However, it is well know that some bactericidal drugs may be bacteriostatic against certain microorganisms and vice versa. These drugs are well known in the art and may be found, for example, in *The Merck Manual of Diagnosis and Therapy*, 13$^{th}$ edition, Section 13, Chapter 153 Anti-bacterial Drugs, 2001, incorporated herein by reference in its entirety.

In another preferred embodiment, the present preferred compositions may be used in combination with an additional pharmaceutical dosage form to enhance their effectiveness in treating a skin disease, disorder, or condition. In this regard, the present preferred compositions may be administered as part of a regimen additionally including any other pharmaceutical and/or pharmaceutical dosage form known in the art as effective for the treatment of a skin disorder. Accordingly, the additional active ingredient or additional pharmaceutical dosage form can be applied to a patient either directly or indirectly, and concomitantly or sequentially, with the preferred compositions described herein.

In one embodiment in this regard, the present preferred composition and the additional pharmaceutical dosage form can be administered to a patient at the same time. In an alternative embodiment, one of the present preferred compositions and the additional pharmaceutical dosage form can be administered in the morning and the other can be administered in the evening.

In another preferred embodiment, the additional pharmaceutical dosage form can be an oral pharmaceutical dosage form. In this regard, the present topical dosage form can be applied to the target area of the patient, prior to, concomitantly with, or after ingestion of the oral medication.

Furthermore, the formulation may be used with other adjunct therapies and treatments, such as pre-washing with common soaps and mild detergents. However, selection is important when treating skin disorders such as acne since antibacterial soaps and abrasive soaps may increase irritation and make it difficult to use follicular drugs. Such follicular drugs may include topical antibiotics and antiseptics, as well as intralesional corticosteroids.

In superficial pustular acne, the topical benzoyl peroxide/ antibiotic/retinoid compositions may be used in combination with one of the follicular drugs.

Sunlight therapy can be useful in combination with the present subject matter. Sunlight is known to cause mild dryness and slight scaling and is usually helpful. Since sunlight is not always available, some benefit may be obtained with a sunlamp.

Another combination therapy involves Azelaic acid cream 20%, which has antiproliferative and antibacterial effects, and is known to be effective in comedonal or inflammatory acne.

An additional combination therapy contemplated with the present compositions is combination with an additional retinoid-containing source, such as for example topical tretinoin (retinoic acid) in 0.025%, 0.05%, or 0.1% cream, 0.05% liquid, or 0.01% or 0.025% gel. Also, a new topical retinoid, Differin® brand adapalene 0.1% gel, Galderma Laboratories, San Antonio, Tex., was recently approved in the United States and may be useful since it may be slightly less irritating than topical tretinoin. Other retinoids which may be useful as an additional retinoid source in combination therapy include Panretin®, containing alitretinoin, and Targretin®, containing bexarotene.

Other topical drugs include OTC drugs, various sulfur-resorcinol combinations, and oral antibiotics may also be helpful in combination with the present compositions when treating superficial pustular acne.

Accordingly a preferred embodiment of the present subject matter additionally relates to a method for the treatment of acne in a patient in need thereof, comprising administering a combination of benzoyl peroxide, antibiotic, and a retinoid to said patient, wherein said combination contains a low level of lincomycin phosphate sulfoxide, lincomycin sulfoxide, clindamycin phosphate sulfoxide, clindamycin sulfoxide, and mixtures thereof.

Methods of Use

The present subject matter also relates to a method for treating a skin disorder or condition in a patient by topically administering to a patient in need thereof one of the above-described topical compositions in an amount effective to treat the skin disorder.

Skin disorders or conditions treatable according to the present methods include but are not limited to microbial infections and inflammation of tissue. The microbial infections can be caused by gram-positive bacteria, gram-negative bacteria, and combinations thereof. Exemplary specific bacteria treatable by the present compositions include but are not limited to *P. acnes, Strep. pyogenes, E. coli, Pseudomonas aeruginosa, Staph. aureus*, and combinations thereof.

Exemplary, non-limiting specific skin disorders, diseases, or conditions treatable by the present topical compositions include but are not limited to acne, impetigo, rosacea, psoriasis, atopic dermatitis, secondary skin infections, responsive dermatoses, and combinations thereof. Other specific skin disorders treatable by the present topical compositions include seborrhea, skin lesions, and bacterial skin infections. In a preferred embodiment, the skin disorder or condition improves following treatment with the present topical compositions.

In a preferred embodiment, the patient to be treated is between the ages of 2 and 45. In a particularly preferred embodiment, the patient to be treated is between the ages of 10 and 35. In yet another preferred embodiment, the patient to be treated is between the ages of 12 and 25.

Process for Preparing

The present subject matter further relates to a process for preparing a topical composition comprising a storage-stable mixture of a benzoyl peroxide suspension, a solution of an antibiotic or a pharmaceutically acceptable salt thereof, and suspension of a retinoid or a pharmaceutically salt thereof.

The present preferred processes can be carried out in various steps. One preferred step requires separately preparing a benzoyl peroxide intermediate composition, a retinoid intermediate composition, and an antibiotic solution, each of which is prepared at a temperature of about 15 to about 30° C.

In a preferred process step, the pH of the benzoyl peroxide intermediate composition may be adjusted before it is mixed with the retinoid intermediate composition and antibiotic solution under conditions sufficient to yield a topical composition having a final pH of between about 3 to about 8. Preferably, the topical composition thus formed comprises sufficient inactive ingredients to provide storage stability and effectiveness for a treatment period.

In an alternative embodiment, the retinoid present in the retinoid intermediate composition can be encapsulated or entrapped in a solid or semi-solid having a melting point at about a mammal's body temperature prior to mixing with the benzoyl peroxide composition and the antibiotic solution. In further alternative embodiments, either of the benzoyl peroxide present in the benzoyl peroxide intermediate composition or the antibiotic present in the antibiotic solution, or any combination of these three or any mixture thereof, can be encapsulated or entrapped in a solid or semi-solid material prior to mixing. This encapsulation or entrapment step can promote the storage-stability of the topical composition.

In a further alternative embodiment, the benzoyl peroxide intermediate composition and the retinoid intermediate composition can be separately milled prior to their mixing with the antibiotic solution.

In a preferred embodiment, the final topical composition made according to the present process will have a viscosity lower than the viscosity of the benzoyl peroxide intermediate composition.

The present processes will preferably result in compositions having benzoyl peroxide impurities or degradates of not more than about 0.25-1.25% by weight, antibiotic impurities or degradates of not more than about 0.01% by weight, and retinoid impurities or degradates of not more than about 0.001% by weight.

These compositions are preferably manufactured to have about 1% to about 3% less water by weight as compared to a topical formulation having one of benzoyl peroxide, an antibiotic, or a retinoid alone, but not both together. Such formulations unexpectedly result in compositions that exhibit less skin sensitivity.

The combinations produced according to these processes can maintain stability for a minimum of one month at room temperature (e.g. 22° C.) and relative, or ambient, humidity.

Routes of Administration/Dosage

To be effective, the route of administration for the topical compositions used in the present methods and pharmaceutical compositions must readily affect the target areas. In particular, acne is known to affect the face, neck, back, ears, and scalp.

Dosage levels for the antibiotics, the benzoyl peroxide, and the retinoid are well known in the art and are selected to maximize the treatment of the above conditions. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results can provide useful guidance on the proper doses for patient administration. Studies in animal models are also helpful. The considerations for determining the proper dose levels are well known in the art and are incorporated herein for the present subject matter.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time are well known in the art.

Lessening exposure by once-daily administration affects multiple pharmacokinetic parameters and provides the initial mechanism for avoiding skin irritation and inflammation and the other toxicity issues discussed herein. Additional formulations may be prepared which factor in the benefit/risk ratio for an antibiotic, benzoyl peroxide, and retinoid composition. The level of toxicity of these compounds is known and reference is made to the package inserts for Cleocin T® and BenzaClin® and the level of adverse events reported from their clinical trials. In particular, BenzaClin® reported having the following events: dry skin (12%), pruritis (2%), peeling (2%), erythema (1%) and sunburn (1%) as compared to vehicle which reported dry skin (6%), pruritis (<1%), peeling (–), erythema (<1%) and sunburn (–), or roughly twice the number of side effects as vehicle.

Since benzoyl peroxide is a keratolytic, i.e. causes softening and swelling of the cells at the surface of the skin so that the outer layer of the skin peels off or can easily be removed, reducing exposure to it reduces irritation. Upon application, the benzoyl peroxide converts to benzoic acid and has antibacterial and anti-fungal properties. Additionally, the low pH of the present formulations may have an additive keratolytic effect on the skin as well as on the anti-bacterial properties. Benzoyl peroxide may also act as a preservative within the formulation. The antibiotic may degrade at pH higher than about 6.5, thus requiring the pH to be maintained below this level, as described herein. The present formulations take these and other factors into account and are manufactured to reduce sensitivity, irritation, and/or inflammation.

It is preferred that the first composition and the second composition of the present subject matter are stored separately prior to application. Still, single dosage kits and packages containing once per day amounts of the present compositions may be prepared. Single dose, unit dose, and once-daily disposable containers of the mixtures and compositions of the present subject matter are contemplated as within the scope of the present subject matter. The single dosage kits and packages may contain separate compartments for holding the benzoyl peroxide-containing composition and the antibiotic/retinoid composition apart from one another. Upon opening the single dose kit or package, the benzoyl peroxide-containing composition and the antibiotic/retinoid composition are mixed prior to or during administration to form the final topical composition.

For example, after a user opens a single dose package of the present subject matter, the user empties the chambers of the package into his or her palm, or into a suitable mixing container, and then mixes the benzoyl peroxide-containing composition with the antibiotic/retinoid composition to form the final topical composition prior to applying the topical composition to the affected area. In an alternative embodiment, the user opens a single dose package of the present subject matter and empties the chambers of the package directly onto the affected area of skin. The benzoyl peroxide-containing composition and the antibiotic/retinoid composition are then mixed as the user rubs the composition into the affected area of skin.

The present topical compositions may be formulated for storage in a substantially non-reactive package to enhance stability of the product. Preferably, the non-reactive package contains at least two storage areas, one to store the benzoyl peroxide-containing composition and one to store the antibiotic/retinoid composition. This new method of storage provides enhanced product stability in comparison with the previous packages. Non-limiting examples of preferred non-reactive packages in this regard include a glass package, a molded or flexible plastic package, a single-dose vial, an aluminum package, a tin package, a composite cardboard package, a laminated package, a laminated pouch, a pump, and a combination thereof. Composite cardboard packages useful in this regard include wax coated cardboard packages.

In preferred embodiments, the benzoyl peroxide-containing composition and the antibiotic/retinoid composition can be stored in the non-reactive package under a blanket of an inert gas. Preferred, non-limiting examples of inert gases useful in this regard include nitrogen gas, argon gas, and a mixture thereof.

Additionally, the use of one of these packaging systems permits the present compositions to be stored such that both the initial benzoyl peroxide-containing composition and the antibiotic/retinoid composition are stable at room temperature. In an alternative embodiment, the initial benzoyl peroxide and antibiotic or retinoid composition requires refrigeration, while the remaining antibiotic or retinoid composition does not.

The amount of composition per single packet may range from about 0.1 mL to about 20.0 mL, preferably between about 0.5 and about 5.0 mL, more preferably between about 1 and about 3 mL.

In a further preferred embodiment, the topical composition of the present subject matter is administered from a dual chambered apparatus containing separate chambers to hold the benzoyl peroxide-containing composition and the antibiotic/retinoid composition. In one example of such an apparatus, a dispenser is able to simultaneously dose the two compositions separately contained in the chambers by pressing a dosing head, which subsequently dispenses the two compositions in approximately equal volumes.

If desired, a dispensing unit that is able to deliver the benzoyl peroxide-containing composition and the antibiotic/retinoid composition in a ratio, such as, for example, 1:2 can be used.

A further embodiment for administering the topical compositions of the present subject matter is a two-compartment tube, with the benzoyl peroxide-containing composition in one compartment and the antibiotic/retinoid composition in the other compartment. It is contemplated that the final topical composition applied from the two-compartment tube contains a particular ratio, for example 2:1 or 1:1, of the benzoyl peroxide-containing composition to the antibiotic/retinoid composition.

In each of the alternative packaging embodiments, the benzoyl peroxide-containing composition and the antibiotic/retinoid composition are mixed just prior to or during administration to form the final topical composition, as is the case with the single dose package embodiment disclosed above. For example, a user dispenses the respective compositions from the chambers of a multi-chambered apparatus into his or her palm, or into a suitable mixing container, and then mixes the benzoyl peroxide-containing composition with the antibiotic/retinoid composition to form the final topical composition prior to applying the topical composition to the affected area. In an alternative embodiment, the user dispenses the respective compositions from the multi-chambered apparatus directly onto the affected area of skin. The benzoyl peroxide-containing composition and the antibiotic/retinoid, composition are then mixed as the user rubs the composition into the affected area of skin.

In another alternative embodiment, the present compositions can be administered using one or more applicators. Non-limiting examples of useful applicators in this regard include a pledget, a swab, a pad, and combinations thereof. Additionally, the present subject matter further contemplates that any of these topical compositions are provided in a package of less than 5 g topical composition as a unit of use.

The ability to formulate compositions capable of long term storage, without pre-mixing or compounding requirements until just prior to application, are also contemplated herein. Specifically, the present compositions remain unexpectedly stable in storage for periods including between about 2 weeks and about 18 months, preferably between about 3 weeks and about 15 months, more preferably between about 30 days and about 24 months.

Once-daily disposable packaging may also improve patient compliance, especially for teenagers.

The stability and effectiveness of the topical preparations may last for at least 1 to 24 months at room temperature, or under refrigeration. This improved stability provides pharmacists and other dispensers of medication with a product which no longer requires compounding at the time of dispensing. Because compounding is no longer required, homogeneity is controlled at the point of manufacture, which improves dosing and ultimately compliance.

Advantageously, the final product requires no compounding by the pharmacist. In addition, compliance with exact amounts is possible with a lessened chance of impurities entering the product and contaminating it.

By maintaining the compositions at the present specific pH, the tendency of benzoyl peroxide to oxidize and degrade the antibiotic and retinoid is largely overcome and the product remains stable during storage at room temperature for extended periods.

The following examples are illustrative of preferred embodiments herein and are not to be construed as limiting the present subject matter thereto. All polymer molecular weights are mean average molecular weights. All percentages are based on the percent by weight of the final delivery system or formulation prepared unless otherwise indicated and all totals equal 100% by weight.

EXAMPLE 1

A benzoyl peroxide-containing composition is prepared, as is a further composition comprising a tazarotene-containing suspension. The benzoyl peroxide-containing composition is then mixed with the tazarotene suspension to prepare a final composition having the following components.

| Ingredient | Percent by Weight |
| --- | --- |
| Benzoyl Peroxide 78% | 6.65 |
| Clindamycin phosphate | 1.28 |
| Purified Water | 86.33 |
| Glycerin | 5.56 |
| Carbomer 940 | 1.11 |
| Sodium Hydroxide | 0.155 |
| Titanium Dioxide | 0.05 |
| Methylparaben | 0.03 |
| Total: | 100.0% |

EXAMPLE 2

A benzoyl peroxide-containing composition is prepared, as is a further composition comprising a tazarotene-containing suspension and a clindamycin solution. The benzoyl peroxide-containing composition and the tazarotene/clindamycin compositions are stored separately in a dual chambered device. The benzoyl peroxide-containing composition is then mixed with the tazarotene suspension/clindamycin solution composition just prior to final use to prepare a final composition having the following components.

| Ingredient | Percent by Weight |
| --- | --- |
| Benzoyl Peroxide 78% | 6.73 |
| Clindamycin phosphate | 1.28 |
| Tazarotene | 0.10 |
| Purified Water | 85.875 |
| Glycerin | 5.00 |
| Carbopol 980 | 0.85 |

-continued

| Ingredient | Percent by Weight |
|---|---|
| Sodium Hydroxide | 0.075 |
| Titanium Dioxide | 0.05 |
| Methylparaben | 0.04 |
| Total: | 100.0% |

EXAMPLE 3

A clindamycin-containing composition is prepared, as is a further composition comprising a tazarotene-containing suspension. The clindamycin-containing composition is then mixed with the tazarotene suspension to prepare a final composition having the following components.

| Ingredient | Percent by Weight |
|---|---|
| Clindamycin phosphate | 1.28 |
| Tazarotene | 0.111 |
| Purified Water | 92.11 |
| Glycerin | 5.56 |
| Carbomer 940 | 0.741 |
| Sodium Hydroxide | 0.114 |
| Titanium Dioxide | 0.0500 |
| Methylparaben | 0.0300 |
| Total: | 100.0% |

EXAMPLE 4

A tazarotene-containing suspension is prepared with a final composition having the following components.

| Ingredient | Percent by Weight |
|---|---|
| Tazarotene | 0.111 |
| Purified Water | 93.56 |
| Glycerin | 5.55 |
| Carbomer 940 | 0.611 |
| Sodium Hydroxide | 0.075 |
| Titanium Dioxide | 0.0500 |
| Methylparaben | 0.0400 |
| Total: | 100.0% |

EXAMPLE 5

A benzoyl peroxide-containing suspension is prepared with a final composition having the following components.

| Ingredient | Percent by Weight |
|---|---|
| Benzoyl Peroxide | 6.65 |
| Purified Water | 87.06 |
| Glycerin | 5.00 |
| Carbomer 940 | 1.10 |
| Sodium Hydroxide | 0.105 |
| Titanium Dioxide | 0.0500 |
| Methylparaben | 0.0400 |
| Total: | 100.0% |

EXAMPLE 6

Tables 1, 2, and 3 show the stability of the combined active ingredients. An analysis was performed on a composition containing 1.06% of benzoyl peroxide, 0.096% of tazarotene, and 1.06% of clindamycin after the two initial compositions are combined. Measurements were taken at the end of 2 weeks. The composition was stored at 2 different temperatures, i.e., 25° C. and 30° C. The levels of benzoyl peroxide, tazarotene, and clindamycin were measured at each temperature. The results are as follows:

TABLE 1

| Benzoyl Peroxide (BPO) (as % w/w): Initial 1.06% | | |
|---|---|---|
| | 25° C. | 30° C. |
| 2 weeks | 1.06 | 1.06 |

TABLE 2

| Tazarotene (as % w/w): Initial 0.096% | | |
|---|---|---|
| | 25° C. | 30° C. |
| 2 weeks | 0.088 | 0.087 |

TABLE 3

| Clindamycin (as % w/w): Initial 1.06% | | |
|---|---|---|
| | 25° C. | 30° C. |
| 2 weeks | 1.06 | 1.05 |

EXAMPLE 7

Tables 4, 5, and 6 show the stability of the active ingredients in a composition containing 5.22% of benzoyl peroxide, 0.103% of tazarotene, and 1.06% of clindamycin after the two initial compositions are combined.

A 2-week analysis of the composition was undertaken following the procedure of Example 2.

TABLE 4

| Clindamycin (as % w/w): Initial 1.06% | | |
|---|---|---|
| | 25° C. | 30° C. |
| 2 weeks | 1.06 | 1.05 |

TABLE 5

| Benzoyl Peroxide (BPO) (as % w/w): Initial 5.22% | | |
|---|---|---|
| | 25° C. | 30° C. |
| 2 weeks | 5.24 | 5.23 |

TABLE 6

| Tazarotene (as % w/w): Initial 0.103% | | |
|---|---|---|
| | 25° C. | 30° C. |
| 2 weeks | 0.098 | 0.088 |

EXAMPLE 8

Tables 7 and 8 show the stability of the active ingredients in a composition containing 0.209% of tazarotene and 2.13% of clindamycin after the two initial compositions are combined.

A 6-month analysis of the composition was undertaken following the procedure of Example 2.

TABLE 7

| Clindamycin (as % w/w): Initial 2.13% | | | |
|---|---|---|---|
| | 25° C. | 30° C. | 40° C. |
| 6 months | 2.07 | 1.96 | 1.74 |

TABLE 8

| Tazarotene (as % w/w): Initial 0.209% | | | |
|---|---|---|---|
| | 25° C. | 30° C. | 40° C. |
| 6 months | 0.206 | 0.206 | 0.205 |

EXAMPLE 9

Tables 9 and 10 show the stability of the active ingredients in a composition containing 5.18% of benzoyl peroxide and 0.099% of tazarotene.

A 2-week and 6-month analysis of the composition was undertaken following the procedure of Example 2.

TABLE 9

| Benzoyl Peroxide (BPO) (as % w/w): Initial 5.18% | | |
|---|---|---|
| | 6° C. | 25° C. |
| 2 weeks | 5.33 | 5.21 |
| 6 months | 5.2 | 5.14 |

TABLE 10

| Tazarotene (as % w/w): Initial 0.099% | | |
|---|---|---|
| | 6° C. | 25° C. |
| 2 weeks | 0.101 | 0.101 |
| 6 months | 0.106 | 0.088 |

EXAMPLE 10

Tables 11 and 12 show the stability of the active ingredients in a composition containing 4.84% of benzoyl peroxide and 1.08% of clindamycin.

A 2-week analysis and 6-month analysis of the composition was undertaken following the procedure of Example 2.

TABLE 11

| Benzoyl Peroxide (BPO) (as % w/w): Initial 4.84% | | |
|---|---|---|
| | 6° C. | 25° C. |
| 2 weeks | 5.53 | 5.01 |
| 6 months | 4.81 | 4.85 |

TABLE 12

| Clindamycin (as % w/w): Initial 1.08% | | |
|---|---|---|
| | 6° C. | 25° C. |
| 2 weeks | 1.04 | 1.05 |
| 6 months | 1.06 | 0.91 |

EXAMPLE 11

Tables 13 and 14 show the stability of the active ingredients in a composition containing 0.105% tazarotene and 1.07% of clindamycin.

A 2-week analysis and 6-month analysis of the composition was undertaken following the procedure of Example 2.

TABLE 11

| Tazarotene (as % w/w): Initial 0.105% | | |
|---|---|---|
| | 6° C. | 25° C. |
| 2 weeks | 0.097 | 0.099 |
| 6 months | 0.101 | 0.102 |

TABLE 12

| Clinamycin (as % w/w): Initial 1.07% | | |
|---|---|---|
| | 6° C. | 25° C. |
| 2 weeks | 1.07 | 1.06 |
| 6 months | 1.06 | 1.02 |

EXAMPLE 12

Table 13 shows the stability of the active ingredient in a composition containing 0.095% of tazarotene.

A 6-month analysis of the composition was undertaken following the procedure of Example 2.

TABLE 13

| Tazarotene (as % w/w): Initial 0.095% | | |
|---|---|---|
| | 6° C. | 25° C. |
| 6 months | 0.102 | 0.105 |

The present subject matter being thus described, it will be obvious that the same may be varied in many ways. Such variations are not to be regarded as a departure from the spirit and scope of the present subject matter, and all such modifications are intended to be included within the scope of the following claims.

We claim:

1. A dual chamber device comprising
   a first storage-stable benzoyl peroxide-containing composition in suspension in a first chamber of the dual chamber device; and
   a second composition comprising clindamycin or a pharmaceutically acceptable salt or ester thereof in solution and a retinoid or a pharmaceutically acceptable salt thereof in a second chamber of the dual chamber device;
   wherein, when dispensed from the dual chamber device, the first composition and the second composition together comprise a topical composition which has a final pH of about 3 to about 8.

2. The dual chamber device of claim 1, wherein the topical composition has a viscosity lower than the viscosity of the benzoyl peroxide-containing composition before mixing with said second composition.

3. The dual chamber device of claim 1, wherein said topical composition is formulated to once-per-day administration at night.

4. The dual chamber device of claim 1, wherein said topical composition has a final pH of about 3.5 to about 5.5.

5. The dual chamber device of claim 1, wherein said first and second compositions take the form of a solution, gel, cream, lotion, suspension, emulsion, ointment, spray, foam, paste, or any combination thereof.

6. The dual chamber device of claim 1, wherein said benzoyl peroxide-containing composition has a viscosity of about 25,000 to about 1,250,000 centipoises.

7. The dual chamber device of claim 1, wherein said topical composition comprises about 0.1% to about 25% by weight of said benzoyl peroxide.

8. The dual chamber device of claim 1, wherein said topical composition comprises about 0.5% to about 3% by weight of said clindamycin or a pharmaceutically acceptable salt or ester thereof.

9. The dual chamber device topical composition of claim 1, wherein said topical composition comprises about 0.01% to about 1.5% by weight of said retinoid.

10. The dual chamber device of claim 1, wherein said retinoid is selected from the group consisting of tazarotene, retinoic acid, tretinoin, isotretinoin, adapalene, bexarotene, alitretinoin, vitamin A, retinol, retinal, retinyl palmitate, retinyl acetate, ethyl 5-(2-(4,4-dimethylthiochroman-6-yl)ethynyl)thiophene-2-carboxylate, 6-(2-4,4-dimethylthiochroman-6-yl)-ethynyl)-3-pyridylmethanol, 2-(2-(4,4-dimethylthiochroman-6-yl)-ethynyl)-5-pyridinecarboxaldehyde, salts thereof, derivatives thereof, and mixtures thereof.

11. The dual chamber device of claim 1, wherein said topical composition further comprises an excipient selected from the group consisting of surfactants, preservatives, emollients, humectants, fluid alkyl alcohols, thickening agents, emulsifiers, suspending agents, pH modifiers/buffering agents, chelating agents, antioxidants, sun filters, derivatives thereof, and mixtures thereof.

12. The dual chamber device of claim 1, wherein said first and second compositions take the form of a gel.

13. The dual chamber device of claim 1, wherein said topical composition further comprises a sun filter.

14. The dual chamber device of claim 13, wherein said sun filter is selected from the group consisting of zinc oxide, titanium dioxide, and mixtures thereof.

15. The dual chamber device of claim 1, wherein one or more of said benzoyl peroxide, said clindamycin or a pharmaceutically acceptable salt or ester thereof, and said retinoid or a pharmaceutically acceptable salt thereof is encapsulated or entrapped in a solid or semi-solid ingredient.

16. The dual chamber device of claim 1, wherein each of the benzoyl-peroxide containing compositions and the retinoid/clindamycin composition is stable at room temperature for a minimum of 6 months when stored separately in a dual chamber package.

17. The dual chamber device of claim 12, wherein said gel comprises a thickener selected from the group consisting of a carbomer, a polyacrylic polymer, cellulosic polymers, such as gum arabic, gum acacia, gum tragacanth, locust bean gum, guar gum, hydroxypropyl guar, xanthan gum, cellulose gum, sclerotium gum, carageenan gum, karaya gum, cellulose gum, rosin, methylcellulose, hydroxyethylcellulose, hydroxypropylcellulose, hydroxymethylcellulose, hydroxypropylmethylcellulose, methylhydroxyethylcellulose, cetyl hydroxyethylcellulose, carboxymethylcellulose, corn starch, hydroxypropyl starch phosphate, distarch phosphate, distarch dimethylene urea, aluminum starch octenyl succinate, maltodextrin, dextran, poly(acrylamide), PEG-150 distearate, PEG-150/decyl alcohol/SMDI copolymer, PEG-150/stearyl alcohol/SMDI copolymer, PEG-180/Laureth-50/TMMG copolymer, Polyether I, acrylic acid/acrylamidomethyl propane sulfonic acid copolymer, acrylate/C10-30 alkyl acrylate crosspolymer, acrylate/beheneth-25 methacrylate copolymer, acrylate/steareth-20 methacrylate copolymer, acrylate/steareth-20 copolymer, acrylate/VA crosspolymer, acrylic acid/acrylonitrogen copolymer, ammonium acryloyldimethyltaurate/beheneth-25 methacrylate copolymer, ammonium acryloyldimethyltaurate/VP copolymer, caprylic/capric triglyceride (and) sodium acrylate copolymer, PVM/MA decadiene crosspolymer, alginic acid, propylene glycol alginate, dimethicone, silica dimethyl silylate, a dimethylacrylamide/acrylic acid/polystyrene ethyl methacrylate copolymer, derivatives thereof, and mixtures thereof.

18. The dual chamber device of claim 12, wherein said thickener is a carbomer.

19. The dual chamber device of claim 1, wherein the retinoid in the second composition is in suspension.

* * * * *

UNITED STATES PATENT AND TRADEMARK OFFICE
CERTIFICATE OF CORRECTION

PATENT NO. : 9,107,844 B2  Page 1 of 1
APPLICATION NO. : 12/223518
DATED : August 18, 2015
INVENTOR(S) : Kathleen L. Clark et al.

It is certified that error appears in the above-identified patent and that said Letters Patent is hereby corrected as shown below:

In The Claims

Claim 18, Column 26, Line 49,

After "of claim" and before ", wherein said"

Please replace "12" with --17--

Signed and Sealed this
Twenty-ninth Day of December, 2015

Michelle K. Lee
*Director of the United States Patent and Trademark Office*